(12) United States Patent
Williams et al.

(10) Patent No.: US 6,210,352 B1
(45) Date of Patent: Apr. 3, 2001

(54) SPLASHPROOF AND ADJUSTABLE LIMB SLEEVE

(76) Inventors: Peggy Williams; David Williams, both of 7533 Briar Rose, Houston, TX (US) 77063

( * ) Notice: Subject to any disclaimer, the term of this patent is extended or adjusted under 35 U.S.C. 154(b) by 0 days.

(21) Appl. No.: 09/133,298

(22) Filed: Aug. 12, 1998

(51) Int. Cl.$^7$ ................................................ A61F 5/00
(52) U.S. Cl. ........................ 602/3; 128/849; 128/856; 128/878
(58) Field of Search .................. 602/3, 20, 23; 128/846, 849, 878

(56) References Cited

U.S. PATENT DOCUMENTS

| | | | |
|---|---|---|---|
| 3,710,790 | 1/1973 | Lemon | 128/165 |
| 3,741,203 | 6/1973 | Liman | 128/165 |
| 4,043,326 | 8/1977 | Little et al. | 128/82 |
| 4,098,268 | 7/1978 | Scott | 128/82 |
| 4,139,003 | 2/1979 | Little et al. | 128/82 |
| 4,157,713 | 6/1979 | Clarey | 128/87 R |
| 4,442,834 | 4/1984 | Tucker et al. | 128/90 |
| 4,523,586 | 6/1985 | Couri | 128/82 |
| 4,530,350 | 6/1985 | Brown et al. | 128/82 |
| 4,562,834 | 1/1986 | Bates et al. | 128/82 |
| 4,639,945 | 2/1987 | Betz | 2/22 |
| 4,727,864 | 3/1988 | Wiesenthal et al. | 128/82 |
| 4,911,151 | 3/1990 | Rankin et al. | 128/82 |
| 5,063,919 | 11/1991 | Silverberg | 128/82 |
| 5,070,541 | 12/1991 | Gloss | 2/16 |
| 5,113,533 | 5/1992 | Takada | 2/17 D |
| 5,143,762 | 9/1992 | Ho | 428/35 |
| 5,173,967 | 12/1992 | Carter | 2/242 |
| 5,187,813 | 2/1993 | Klein | 2/16 |
| 5,395,302 | 3/1995 | Botha et al. | 602/3 |
| 5,511,241 | 4/1996 | Ziegler | 2/2.5 |

*Primary Examiner*—Michael A. Brown
*Assistant Examiner*—Lalita M. Hamilton

(57) ABSTRACT

This limb sleeve is a splashproof sleeve that is donned on the limbs. The sleeve is made from a hydrophobic material which absorbs moisture and perspiration on the skin and also repels moisture from the outside. The sleeve utilizes a unique silicone seal which is able to conform to any contour and is adjustable. One seal is sewn to each end of the protective sleeve to provide a splashproof closure between the limb and sleeve. The longitudinal ends of the sleeve are held in place by a hook and loop fastener. The patient can either wrap the sleeve around the limb and secure the longitudinal ends with the hook and loop fastener or partially fasten the large end of the sleeve and draw the sleeve over the limb until the sleeve fits tightly against the limb. Then the longitudinal joint and lower seal is fastened using the hook and loop fastener. Bathing, weather, and sweating are the primary sources of moisture. This invention shields the limb from outside moisture and absorbs sweat on the inside, thus protecting bandages and medical devices.

12 Claims, 5 Drawing Sheets

Figure 1:
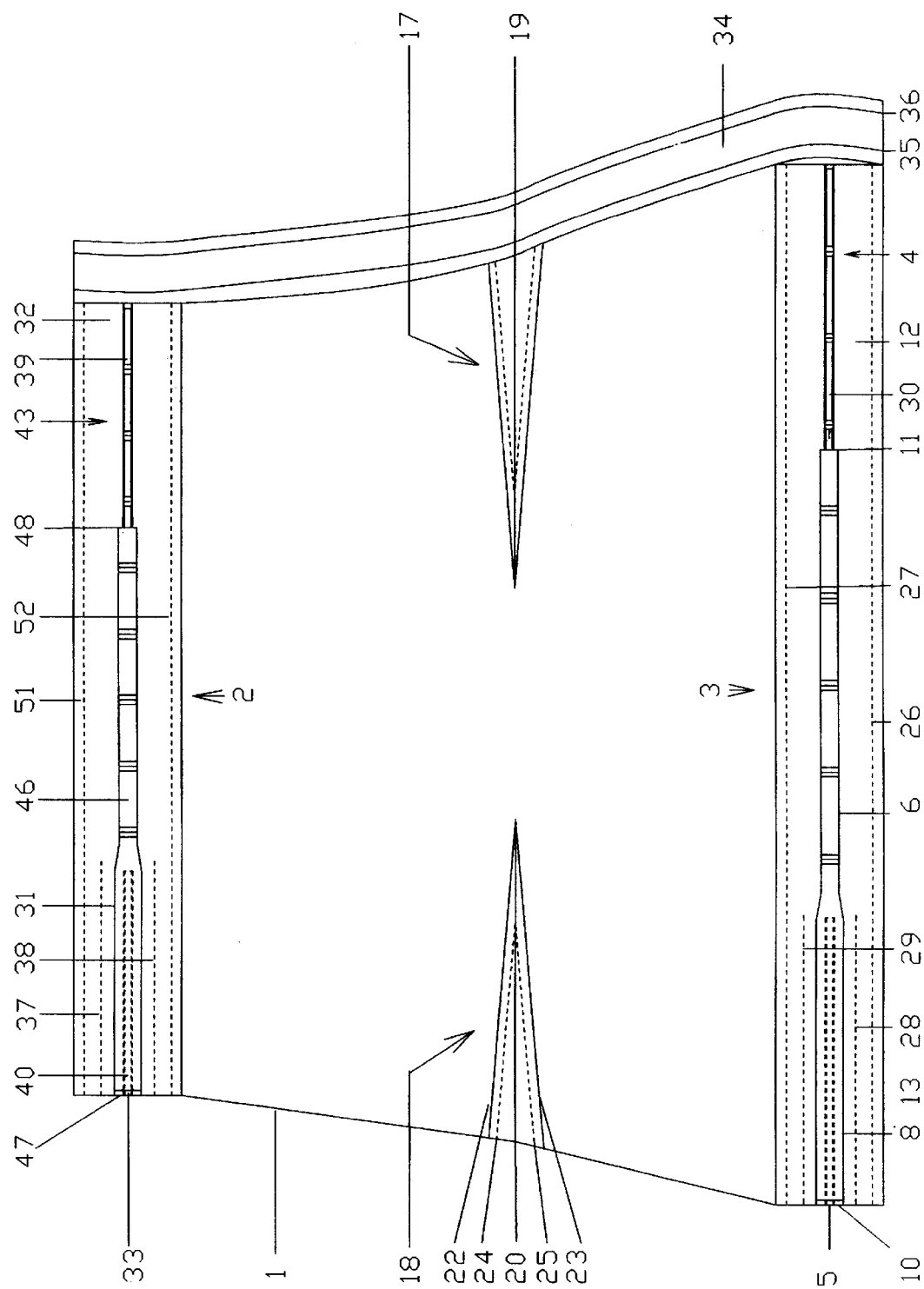

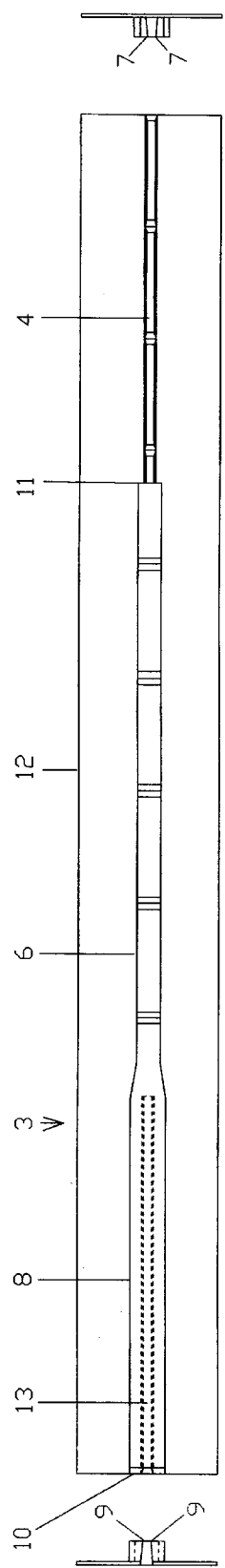
Figure 2
Figure 7
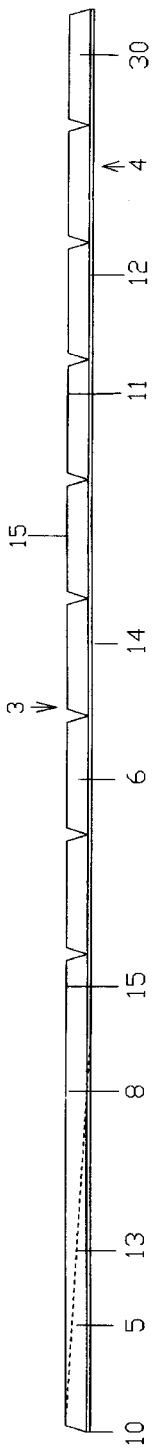
Figure 8
Figure 3

SPLASHPROOF AND ADJUSTABLE LIMB SLEEVE

BACKGROUND—FIELD OF INVENTION

This invention relates to the medical or sports profession specifically, to an improved splashproof limb protection device.

BACKGROUND—DISCUSSION OF PRIOR ART

To design an acceptable splashproof device a number of design constraints must be satisfied. The term splashproof as used in this specification means that when the device is exposed to the weather or bathing, the area to be protected will remain dry. First, the seal between the limb and the outer covering must not choke the blood supply. The seal must maintain contact with the skin in spite of the motility of the body part. The seal must be adjustable to accommodate varying limb sizes. The device must be simple to manufacture. And finally, the device must have an aesthetic quality.

Sealing methods are usually accomplished by (1) straps and cords circumventing a flexible outer material, (2) straps and cords circumventing a flexible outer material with an internal spongy material, (3) deformable rings, and (4) inflatable boots.

Some of the more common methods utilizing straps and cords circumventing a flexible outer material are described in U.S. Pat. No. 4,911,151 Disposable Dressing Cover to Rankin(1990), U.S. Pat. No. 4,727,864 Protective Sleeve for the Leak-proof Coverage of Body Parts to Wiesenthal (1988), U.S. Pat. No. 5,063,919 Protective Sleeve to Silverberg(1991), U.S. Pat. No. 4,530,350 Limb Protective Covering to Brown(1985), U.S. Pat. No. 4,523,586 Protective Cover For a Limb or a Cast to Couri(1985), and U.S. Pat. No. 4,562,834 Waterproof Limb Covering to Bates (1986).

U.S. Pat. No. 3,741,203 Protective Covering to Liman (1973) describes a method using straps and cords circumventing a flexible outer material with an internal spongy material.

Methods using deformable rings and inflatable boots are described in U.S. Pat. No. 4,639,945 Protective Method and Apparatus to Betz(1987), U.S. Pat. No. 4,139,003 Waterproof Cast Protector to Little(1979), U.S. Pat. No. 4,043,326 Waterproof Cast Protector to Little(1977).

Before a tight joint can be achieved, all of the possible routes for leakage must be removed by a force of such magnitude so as to remove the minute irregularities between the seating surface and the gasket surface. For all gaskets, there is a minimum seating pressure. With regard to the prior art, all these contraptions use various methods for sealing. First, the outer flexible material is pressed against the skin by the application of straps and cords. In this case the flexible material is the seating surface, and the skin is the gasket. As the flexible material is brought closer to the skin by tightening the strap or cord, the flexible material becomes bunched and uneven causing the minimum seating pressure to increase. In order that this method seal, the skin must be squeezed into the irregularities of the flexible material by increasing the tension of the strap, causing discomfort to the user. Consequently, these types of joints either leak or cause discomfort to the user.

Attaching a spongy material to the inner circumference of the flexible covering is another method used by these devices. In this case the spongy material is the gasket, and the skin is the seating surface. The idea is to provide a soft material such as a gasket which, under the application of the strap, flows into the irregularities of the skin. This is self defeating because the spongy material is probably not as soft as the skin and, also, the spongy material will have a large number of surface irregularities. The irregularities of the seal are increased because the texture of the material has irregularities and, in addition, the pleating of the material as the strap is tightened. For this joint to seal, the tension in the strap must be increased to squeeze the skin into the pleats and fill voids of the spongy material. This method is probably better than trying to squeeze the skin into the flexible covering but the seal will leak or cause discomfort to the user. As this joint ages, the resilience of the spongy material will decrease and, as a consequence, the strap tension must be increased to obtain the same watertightness.

With regard to the deformable ring sealing device, if the limb were of cylindrical shape, this seal would probably hold. However, since limbs are usually unsymmetrical in cross section, this seal is not adequate for the intended use. For persons fitted with catheters or bandages, shoving the limb through this deformable material could cause damage to the catheter and grief to the user.

The inflatable boot is probably the best of all of these contraptions since the limb and catheter can be maneuvered through the opening and afterward the seal inflated. This seal is not much different than the strap and flexible material discussed above except the strap has been replaced with air pressure. The skin still has to be squeezed into the boot material irregularities. This joint will either leak or cause discomfort to the user.

All of these contraptions try to reduce the larger circumference of the outer covering to the smaller circumference of the limb causing the material to pleat which undermines the best of these innovations.

Since some of the prior art references use more than one turn of the strap to encompass the flexible material, this suggests that the area of the joint should be increased. This seems reasonable, since the irregularities are random in nature: the more turns, the higher the likelihood the joint will seal. But as the turns are increased, the tension must increase or the presiding turns will slacken. This increase in the surface area with its attending increase in the strap tension will seal the joint but will cause grief to the wearer.

Objects and Advantages

My protective sleeve has numerous advantages. First, the sleeve is made from a hydrophobic cloth which absorbs smaller amounts of water than wool, cotton or silk. This allows perspiration to wick to the outside and evaporate. At the same time, the cloth has an impenetrable barrier which repels rain and droplets of water. The sleeve has a unique seal that is adjustable and also eliminates the pleating or bunching of the outer fabric. One seal can accommodate a large variation of limb sizes. In addition, the fabric has a hook and loop substitute laminated to the outside of the hydrophobic cloth which eliminates the stiff backing material associated with most hook and loop designs. The result is a flexible sleeve that is comfortable to the patient. The sleeve can be adjusted or installed without the help of another person. The sleeve does not crawl or shift along the limb due to the motion of the limb. The sleeve is lightweight, soft, and non-chafing. With the hook and loop substitute laminated to the outside of the hydrophobic cloth used in this invention, additional paraphernalia associated with the medical treatment of cancer such as tubes and pumps can be fastened to the sleeve.

DRAWING FIGURES

Figure 4:
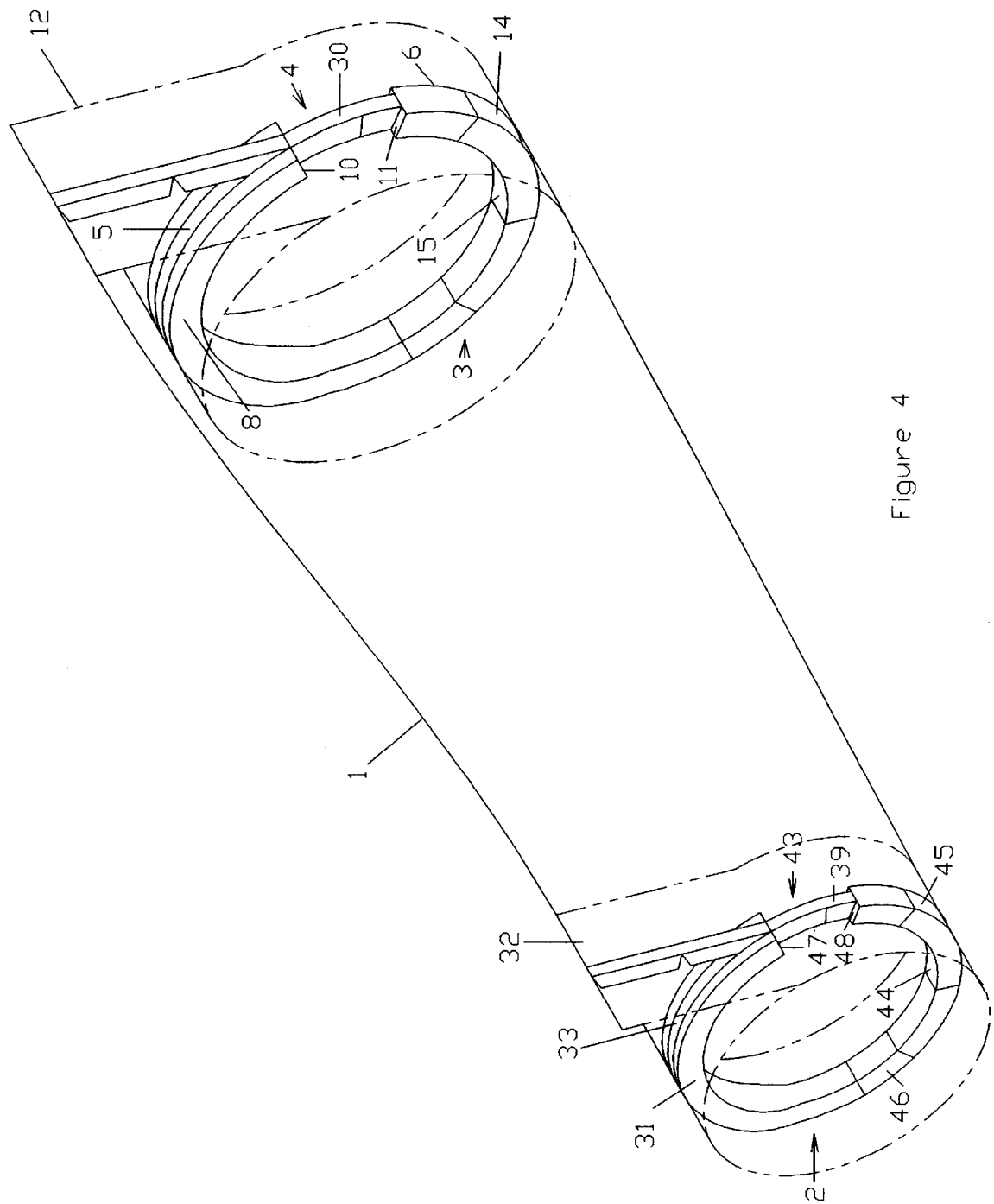
Figure 5:
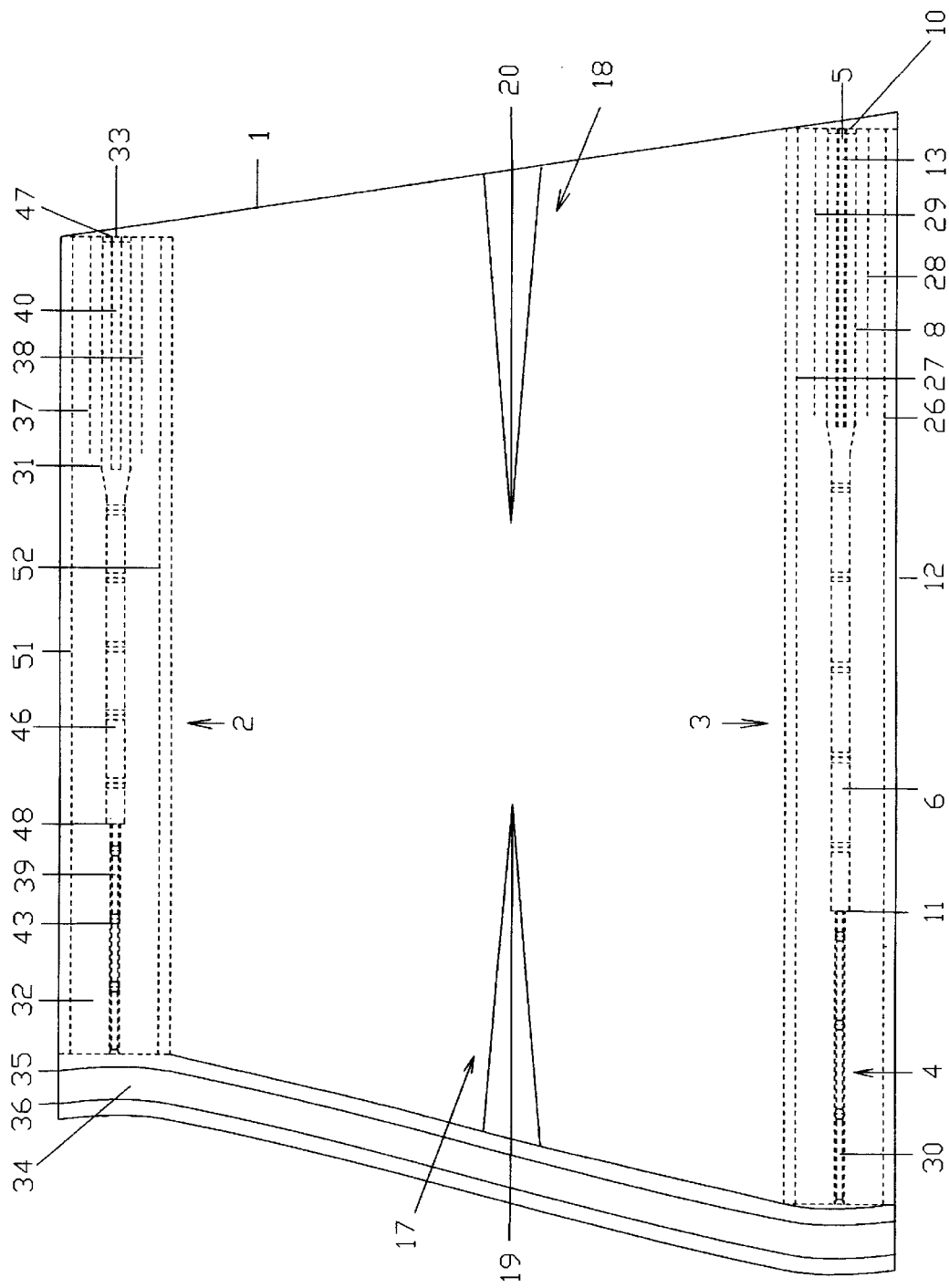
Figure 6:
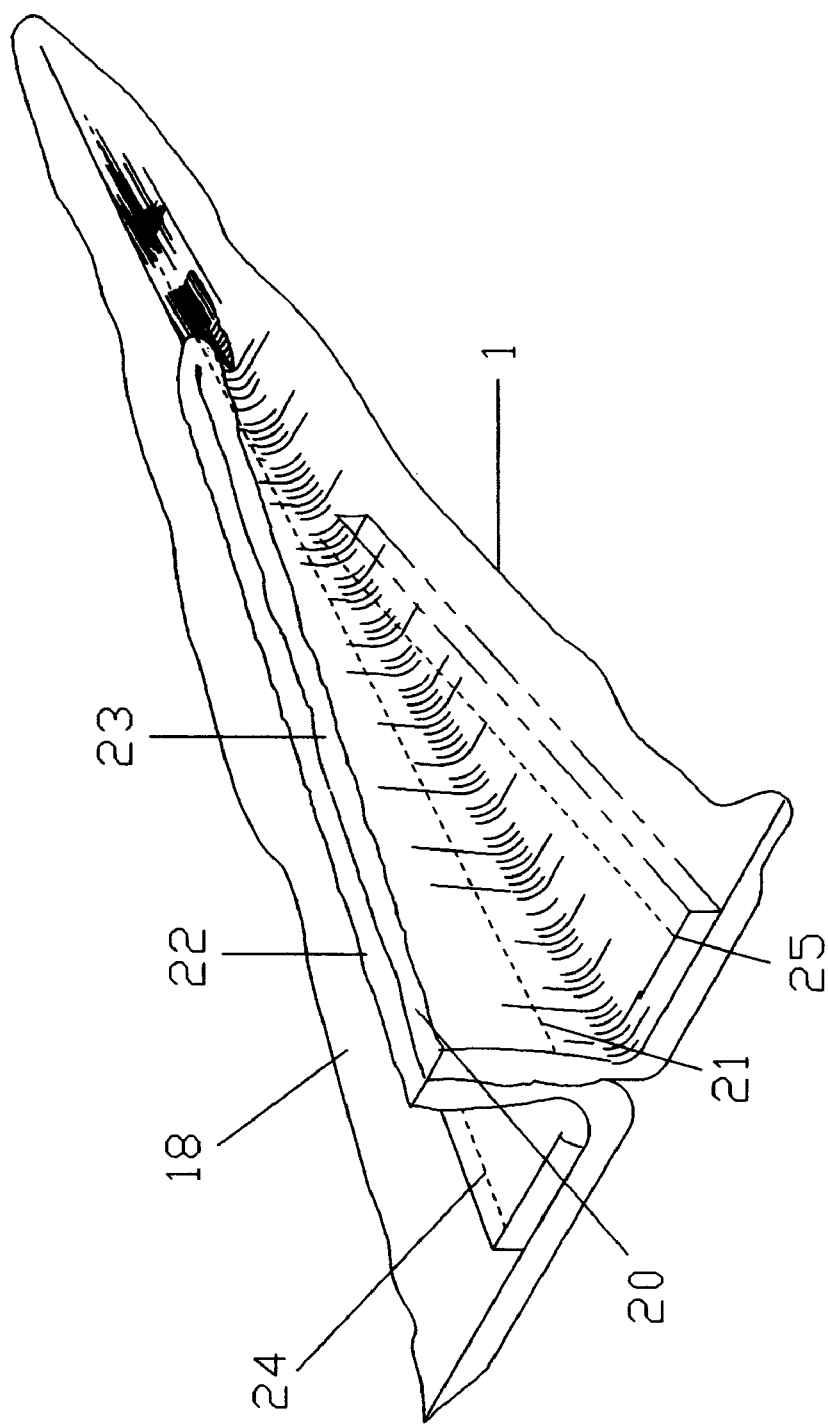

FIG. 1 Plan view of the limb side of open limb sleeve
FIG. 2 Plan view of male seal
FIG. 3 Side view of male seal
FIG. 4 Isometric view of installed limb sleeve
FIG. 5 Plan view of the outside of open limb guard
FIG. 6 Isometric view showing dart of sleeve
FIG. 7 End view of plinth of upper arm seal
FIG. 8 End view of rib of upper arm seal

REFERENCE NUMERALS IN DRAWING

1. Cloth of limb sleeve
2. Forearm seal
3. Upper arm seal
4. Rib of upper arm seal
5. Groove of upper arm seal
6. Thicker wedge of upper arm seal
7. Cross-sectional taper of rib of upper arm seal
8. Plinth of upper arm seal
9. Cross-sectional taper of plinth of upper arm seal
10. Section 1 of upper arm seal
11. Section 2 of upper arm seal
12. Web of upper arm seal
13. Bottom of groove of upper arm seal
14. Bottom of upper arm wedge
15. Top of upper arm wedge
17. Dart one
18. Dart two
19. Cut one for dart one
20. Cut two for dart two
21. Stitch to fastened piece one of dart to piece two of dart
22. Piece one of dart
23. Piece two of dart
24. Stitch to fasten piece one of dart to cloth of limb sleeve
25. Stitch to fasten piece two of dart to cloth of limb sleeve
26. Stitch to fasten upper arm seal to cloth
27. Stitch to fasten upper arm seal to cloth
28. Stitch to fasten plinth of upper arm seal to cloth
29. Stitch to fasten plinth of upper arm seal to cloth
30. Thin wedge profile of upper arm seal
31. Plinth of forearm seal
32. Web of forearm seal
33. Groove of forearm seal
34. Hook of hook and loop fastener
35. Stitch to fasten hook of hook and loop fastener to cloth
36. Stitch to fasten hook of hook and loop fastener to cloth
37. Stitch to fasten plinth of forearm seal to cloth
38. Stitch to fasten plinth of forearm seal to cloth
39. Thin wedge profile of forearm seal
40. Bottom of groove of forearm seal
43. Rib of forearm seal
44. Top of forearm wedge
45. Bottom of forearm wedge
46. Thicker wedges of forearm seal
47. Section 1 of forearm seal
48. Section 2 of forearm seal
51. Stitch to fasten forearm seal to cloth
52. Stitch to fasten forearm seal to cloth

DESCRIPTION FIG. 1 THROUGH FIG. 6

This particular sleeve extends from the upper arm to lower arm. FIG. 4 is an isometric view of the limb sleeve as it might look in the installed position with the forearm and upper arm nearly in a straight line. Table 1 and Table 2 summarize the data given in *Humanscale* 7/8/9 (Humanscale 7/8/9 is a registered trademark) by

TABLE 1

| | MALE MEASUREMENTS | | | | |
|---|---|---|---|---|---|
| | SIZE | | | OVERALL LENGTH | LENGTH BETWEEN |
| LOCATION | SMALL (IN) | MEDIUM (IN) | LARGE (IN) | OF SEAL (IN) | SECTION 1 and SECTION 2 (IN) |
| FOREARM | 3.2 | 3.7 | 4.1 | 14.45 | 11.62 |
| | | | | | (11 5/8) |
| UPPER ARM | 3.3 | 3.9 | 4.7 | 16.33 | 11.93 |
| | | | | (16 5/16) | |

TABLE 2

FEMALE MEASUREMENTS

| LOCATION | SIZE | | | OVERALL LENGTH OF SEAL (IN) | LENGTH BETWEEN SECTION 1 and SECTION 2 (IN) |
| --- | --- | --- | --- | --- | --- |
| | SMALL (IN) | MEDIUM (IN) | LARGE (IN) | | |
| FOREARM | 2.7 | 3.0 | 3.5 | 12.56 | 10.05 (10 1/16) |
| UPPER ARM | 2.8 | 3.3 | 3.9 | 13.82 (13 13/16) | 10.36 |

TABLE 3

| DIMENSION | LENGTH OF SEAL | |
| --- | --- | --- |
| | LONG (16 5/16 IN) | SHORT (13 13/16 IN) |
| TOP OF WEDGE | 1.22 IN | 1.02 IN |
| BOTTOM OF WEDGE | 1.35 IN | 1.15 IN |

Diffrient and others. Table 1 gives the dimensions of forearms and upper arms for different sizes of males and Table 2 gives the dimensions of forearms and upper arms for different sizes of females. The sleeve must be large enough to clear a central vein catheter (CVC) or other device when installed on the arm. The sleeve should not interfere with the physiology and comfort of the user; therefore, a generous space between the limb and sleeve should be provided. A central vein catheter is a small, soft tube that is inserted through the skin and into a vein of the patient's arm. A short length of the tube called the extension with a heparin cap, a plastic connector, and a pinch connector is left outside the forearm for the purpose of infusing intravenous products and flushing the inside of the catheter with saline solution. The CVC is stitched to the forearm and covered with bandages. This particular sleeve assumes a value of ¼ inch between the limb and cloth of limb sleeve item 1 so that the sleeve will not interfere with the exogenous portion of the CVC and will also allow the arm to bend. Therefore ½ inch should be added to the values found in columns 2, 3, and 4 of Table 1 and Table 2. For the male sizes (Large dimension of upper arm+½)*PI*=Length of male seal The large dimension of the male upper arm see Table 1 is 4.7 inches which sets the overall length of the male seal at 16 5/16 inches to the nearest 1/16 inch. This value is found in column 5 of Table 1. The small dimension of the male forearm is 3.2 inches. For the male sizes (Small dimension of forearm +½)*PI*=Length between section 1 and section 2

FIG. 1, FIG. 2, FIG. 3, FIG. 4, or FIG. 5 shows a section 1 item 10 and a section 2 item 11. The dimension between section 1 and section 2 is 11 5/8 inches to the nearest ⅛ inch. This value is tabulated in column 6 of Table 1. Also shown in these same figures is a rib item 4 which is 4 11/16 inches long. By varying the length of the rib that is inset into a groove item 5, all male forearm and upper arm sizes can be accommodated.

For female sizes (Large dimension of upper arm+½)*PI*=Length of female seal

The largest dimension of the female upper arm see Table 2 is 3.9 inches which sets the overall length of the female seal at 13 13/16 inches to the nearest 1/16 inch. This value is tabulated in column 5 Table 2. The small dimension of the female forearm is 2.7 inches.

(Small dimension of forearm+½)*PI*=Length between section 1 and section 2

FIG. 1, FIG. 4, or FIG. 5 shows a section 1 item 47 and a section 2 item 48. The dimension between section 1 and section 2 is 10 1/16 inches to the nearest ⅛ inch. This value is tabulated in column 6 of Table 2. Also shown in these same figures is a rib item 43 which is 3¾ inches long. By varying the length of the rib that is inset into a groove item 33, all female forearm and upper arm sizes can be accommodated.

Since the overall length of the seals have been determined, (3) options are available to fabricate a limb sleeve namely, use (2) male seals, use (2) female seals, or (1) male seal and (1) female seal. This particular sleeve uses the latter option. By using a female and a male seal, the size range of the sleeve will overlap into both the male and female sizes shown in Table 1 and Table 2. A male seal item 3 will don the upper arm while a female seal item 2 will be used on the forearm.

The seal has a unique adjustment feature. FIG. 4 shows rib item 4 (or item 43) inset into groove item 5 (or item 33) of upper arm seal item 3 (or item 2). By varying the amount of the inset, the seal can be adjusted to a range of limb sizes. Rib item 4 of seal item 2 (or item 3) includes all thin wedge sections item 30 (or item 39). The rib of male seal item 3 has a length of 4 11/16 inches and the rib of female seal item 2 has a length of 3¾ inches. FIG. 8 shows a taper item 7 integral to rib item 4 (typical for item 43) of upper arm seal item 3 (or item 2). Rib item 4 has a taper for this particular seal of (5) degrees. FIG. 7 shows a plinth item 8 (typical for item 31) which also has a taper item 9 of (5) degrees. When the rib is inset into the groove of the plinth, the tapers provide a interference fit which prevent leakage between the groove and rib. Rib item 4 (or item 43) for this seal is ⅛ inch wide at its base. FIG. 1, FIG. 2, FIG. 3, FIG. 4, or FIG. 5 show a web item 12 (or item 32) which extends on both sides of the centerline of the seal approximately ¾ inches. The web is integral with the plinth, wedges, and rib. The purpose of the web is provide a means of attaching the seal to the cloth with stitches. Each seal item 2 (or item 3) has (8) wedge shape profiles made from either a thicker wedge item 6 (or item 46) or from thin wedges item 30 (or item 39). The purpose of the wedge shape profile is to remove material from the inner circumference. If material were not removed from the inner circumference, as the seal is donned around the limb, the excess material would cause the seal to stiffen and consequently would not allow the seal to conform to the profile of the limb. The wedges of rib item 8 (or item 43) and the wedges between the plinth and rib allow the seal to deform to the irregularities of the many diverse limb sizes.

Referring to FIG. 3 and FIG. 4, the thick wedges of both seals are ¼ inch wide and the length of a side item 14 (or item 45) which is parallel to a contrary side item 15 (or item 44) are shown in Table 3. The bottom length of wedge item 14 (or item 45) is found by dividing the overall length of seal by (12). The top length of wedge item 15 (or item 44) is found by dividing the overall length by PI (=3.14) which results in the outside diameter and from the outside diameter subtract ½ inch which leaves the inside diameter. The inside diameter is multiplied by PI (=3.14) which gives the inside circumference which is divided by (12) to give the top length of wedge item 15 (or item 44). The ½ inch is the amount added to the limb dimension in order that the sleeve clear the medical device. The number of wedges, the width of rib, the width of thicker wedges, and the width of the web were all arbitrarily chosen. Increasing the number of wedges will add to the functionality of the sleeve. There is probably an optimum number of wedges based on cost of the mold, material, and the dimensions of the limb. The plinth with its groove is inherently flexible and for this reason, wedges were not included in this section of the profile. Referring to FIG. 3, the groove of plinth item 8 (or item 31) has (2) sides and a bottom item 13 (or item 40) which tapers from outside edge item 10 (or item 47) along the length seal and ends at web item 12 (or item 32). The length of the taper was chosen arbitrarily. When the seals don the limb and rib item 4 and rib item 43 are inset into groove item 5 and groove item 33 respectively, the rib will almost be flush with the inside circumference of the seal. The purpose of the taper is to eliminate any gap between the limb and seal. The plinth is the wider section of the seal in order that end of the seal section 1 item 10 (or item 47) is not too flimsy. The taper of the bottom of the groove not only allows the rib to merge smoothly with the inner circumference but also adds strength to the section as it tapers upward to the outside.

Rib item 4 (or item 43), thicker wedges item 6 (or item 46), plinth item 8 (or item 31), and web item 12 (or item 32) are all integral. The seals are made from silicone rubber using the injection molding process. Injection molding is a process where thermoplastic molding compounds are plasticized in an appropriate heating cylinder, then forced by plunger action through one or more orifices into a relatively cool mold where the material solidifies to the desired shape. The mold cavity is divided into (2) parts which are held together by a hydraulic ram. After the material solidifies, the mold is parted and the silicone profile see FIG. 2 and FIG. 3 is removed. The mold is closed and the process repeated.

Referring to FIG. 1 and FIG. 5, cloth item 1 is cut into a trapezoidal shape from a piece of cloth furnished by Starensier of Newburyport, Mass. This fabric is breathable and waterproof. The fabric wicks perspiration from the skin to the outside and at the same time provides an impenetrable barrier to rain and droplets of water. Laminated to the outside of this cloth is a hook and loop substitute which will eliminate the stiff backing associated with the standard hook and loop design and will also provide the adjustment means for the sleeve. The sleeve's wear properties, specifically, comfort to the patient are enhanced with the addition of the hook and loop substitute. The cloth is extended approximately 1 inch beyond rib item 4 (or item 43) of each seal in order that the hook of the hook and loop fastener can be sewn to the cloth.

FIG. 1 and FIG. 5 show a dart item 18 contrary to a dart item 17. As the centerlines of the limbs that attach to the elbow are usually at an angle to each other, the purpose of the dart is to deform the surface of the sleeve by removing material so that the sleeve resembles the natural shape of the limbs and elbow. FIG. 6 is an isometric view of one dart item 18 which will help show how a seamstress would make this piece. This drawing is also typical for dart item 17. Referring to FIG. 1, a cut item 19 and a cut item 20 are made along the circumference of the sleeve. The length of the cut will depend on how much the surface of the sleeve is to be deformed and the keen eye of the seamstress. After cut item 20 is made, FIG. 6 shows a piece of cloth item 22 and a piece of cloth item 23 of dart two item 18 pulled together with the ends pointed radially toward the limb and fastened with a stitch item 21. The (2) pieces of cloth are more or less triangular in shape. This removes the largest amount of material from the outside edge of cloth item 1 and to a lesser degree at all other points along cut item 20. Afterwards, piece one item 22 and piece two item 23 are folded over pivoting around stitch item 21 so that they lie against the inner surface of cloth item 1. The final position is shown as phantom lines in FIG. 6. Piece one item 22 is attached to cloth item 1 by a stitch item 24 and piece two item 23 is attached to cloth item 1 by a stitch item 25.

Forearm seal item 2 is attached to cloth item 1 by a plurality of stitches item 51, item 52, item 37, and item 38.

Upper arm seal item 3 is attached to cloth item 1 by a plurality of stitches item 26, item 27, item 28, and item 29.

A hook of the hook and loop item 34 is fastened to the by a plurality of stitches item 35 and item 36.

This completes the fabrication of the protective limb sleeve.

Operation

The sleeve is wrapped around the limbs and positioned to suit the user. Forearm seal item 2 will be located somewhere on the forearm and upper arm seal item 3 will fall on the upper arm. The forearm seal rib item 4 is inset into the forearm seal groove item 5. To eliminate leakage around the limb, the seal must be tight around the limb, and this is accomplished by varying the length of the rib that is inset into the groove. The longitudinal joint is partially fastened by mating hook item 34 to the substitute hook and loop that is laminated to the outside of the cloth. The upper arm seal's rib item 37 is inset into the upper arm groove item 38 and tightened around the limb to prevent leakage. By pressing on the sleeve's hook item 34, the sleeve is secured to the limbs.

Conclusions, Ramifications, and Scope of Invention

Thus the reader will see that this limb sleeve provides a comfortable, flexible, adjustable, and easily manufactured device which can be used to protect a permanent medical device installed on the body such as a central vein catheter.

While my above description contains many specifics, these should not be construed as limitations, but rather as an exemplification of one preferred embodiment thereof. Many variations are possible. For example, the elastic bands, ties, and knit cuffs used to secure the cuffs of cleanroom garments, raincoats, coveralls, disposable sleeve protectors, and slicker suits to the arms and legs could be replaced with the adjustable seal. Mittens and gloves that extend from the hand to the upper arm could be made splashproof by using the adjustable seal. Cast protectors, arm sleeves, shoe covers, hair nets, and garments that must be splashproof could use the adjustable seal. The seal could be dovetailed with lids and caps to cover tanks, bottles, and containers. The seal has been shown molded with a wedge profile but the profile could be solid without wedges. The seal could be made hollow with a thin outer silicone surface such as found in bubble seal packing material. This arrangement would not only allow the seal to conform easily to the shape of the limb due to the cushioning of the entrapped air but also lighten the sleeve by removing material from the inside. The hook and loop provided by manufacturers is not watertight. One method that may be used to seal the hook and loop fastener is to split hook item 34 into (2) pieces and place a thin silicone strip the same length as the hook between the (2) pieces. One piece of split hook item 34 is stitched to the outside edge of cloth item 1, the silicone is placed contiguous to the first piece and stitched to the cloth and finally the last piece of split hook item 34 is placed contiguous to the silicone and stitched to the cloth. The silicone can be slightly thicker than the hook. The seal's groove item 5 and rib item 4 could be replaced with a lap type joint where the ends are placed side by side.

Accordingly, the scope of the invention should be determined not by the embodiment illustrated, but by the appended claims and their legal equivalents.

What is claimed is:

1. A limb sleeve to protect medical devices comprising:
   a plurality of resilient seals, each having a plurality of shapes and an end of said seal having an adjustable joining means that can mate with the plurality of said shapes that form a second end of said seal when said seal is wrapped around a limb with said shapes contacting the limb and said second end is joined to said end by means of said adjustable joining means, and a piece of fabric shaped such that one of said resilient seals can be attached to an edge of said fabric, another said resilient seal can be attached to a contrary edge of said fabric, and a remaining edge is fastened to a closing edge by an adjustable fastening means whereby the adjustable fastening means is a groove and rib joint.

2. The limb sleeve of claim 1 wherein said piece of fabric is selected from the group consisting of nylon, wool, polyester, cotton, and plastics whereby said piece of fabric absorbs moisture.

3. The limb sleeve of claim 1 wherein said piece of fabric is selected from the group consisting of fabrics produced from hydrophobic and hydrophilic fibers, fabrics coated with breathable polyurethane coatings, laminated fabrics which incorporate hydrophobic fibers and hydrophilic fibers, and tightly woven fabrics whereby said piece of fabric is hydrophobic and/or hydrophilic.

4. The limb sleeve of claim 1 wherein said plurality of resilient seals is selected from the group consisting of silicone rubber, plastics, nylon, hydrophobic material, hydrophilic material, and foam whereby said seal will conform to the limb without pleating or bunching the material.

5. The limb sleeve of claim 1 wherein said adjustable joining means is a lap joint whereby the perimeter of the joint can change with varying limb sizes.

6. The limb sleeve of claim 1 wherein said adjustable fastening means is selected from the group consisting of flexible zippers, press type plastic fasteners, pleats, dual lock, and hook and loop whereby the longitudinal joint is adjustable.

7. A limb sleeve to protect medical devices comprising:
   a plurality of resilient seals, each having an end with an adjustable joining means that can mate with a second end of said seal when said seal is wrapped around a limb and said second end is joined to said end by means of said adjustable joining means, and a piece of fabric shaped such that one of said resilient seals can be attached to an edge of said fabric, another said resilient seal can be attached to a contrary edge of said fabric, and a remaining edge is fastened to a closing edge by an adjustable fastening means whereby the adjustable fastening means is a groove and rib joint.

8. The limb sleeve of claim 7 wherein said piece of fabric is selected from the group consisting of nylon, wool, polyester, cotton, and plastics whereby said piece of fabric absorbs moisture.

9. The limb sleeve of claim 7 wherein said piece of fabric is selected from the group consisting of fabrics produced from hydrophobic and hydrophilic fibers, fabrics coated with breathable polyurethane coatings, laminated fabrics which incorporate hydrophobic fibers and hydrophilic fibers, and tightly woven fabrics whereby said piece of fabric is hydrophobic and/or hydrophilic.

10. The limb sleeve of claim 7 wherein said plurality of resilient seals is selected from the group consisting of silicone rubber, plastics, nylon, hydrophobic material, hydrophilic material, foam, and bubble wrap whereby said seal will conform to the limb without pleating or bunching the material.

11. The limb sleeve of claim 7 wherein said adjustable joining means is a lap joint whereby the perimeter of the joint can change with varying limb sizes.

12. The limb sleeve of claim 7 wherein said fastening means is selected from the group consisting of flexible zippers, press type plastic fasteners, pleats, dual lock, and hook and loop whereby longitudinal joint is adjustable.

* * * * *